United States Patent [19]
Hartmann et al.

[11] B 3,993,670
[45] Nov. 23, 1976

[54] BENZODIFURAN COMPOUNDS

[75] Inventors: Peter Hartmann, Cologne-Stammheim; Hans Theidel, Leverkusen, both of Germany

[73] Assignee: Bayer Aktiengesellschaft, Leverkusen, Germany

[22] Filed: Feb. 8, 1974

[21] Appl. No.: 440,858

[44] Published under the second Trial Voluntary Protest Program on February 3, 1976 as document No. B 440,858.

[30] Foreign Application Priority Data
Feb. 9, 1973   Germany............................ 2306515

[52] U.S. Cl. ................ 260/346.2 M; 260/343.2 R; 260/247.2 A; 260/293.58; 252/301.32
[51] Int. Cl.² ........................................ C07D 307/84
[58] Field of Search ............................ 260/346.2 M

[56] References Cited
UNITED STATES PATENTS

| | | | |
|---|---|---|---|
| 3,859,350 | 1/1975 | Sahm et al. | 260/346.2 R |
| 3,864,333 | 2/1975 | Sahm et al. | 260/346.2 M |

OTHER PUBLICATIONS
Grinev et al., *Chem. Abstracts*, vol. 51 (1957), 7350c.

*Primary Examiner*—Henry R. Jiles
*Assistant Examiner*—Bernard I. Dentz
*Attorney, Agent, or Firm*—Plumley and Tyner

[57] ABSTRACT

Benzodifuran compounds of the formula

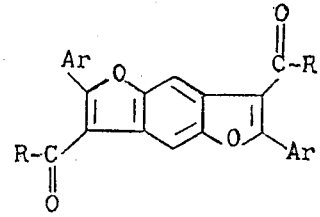

wherein
R represents alkoxy, aralkoxy, aryloxy, cycloalkoxy, hydroxyl, an oxygen atom linked to the radical Ar, or the group

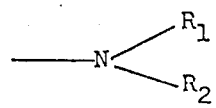

$R_1$ and $R_2$ independently of one another denote hydrogen, alkyl, aralkyl or aryl, or together denote a saturated carbocyclic or heterocyclic ring and Ar denotes an aromatic-carbocyclic or aromatic-heterocyclic radical, with the proviso that Ar denotes a substituted benzene radical if R represents $C_1$-$C_2$-alkyl, are suitable as optical brightening agents and UV-absorber for organic materials.

2 Claims, No Drawings

BENZODIFURAN COMPOUNDS

The invention relates to benzodifurane compounds of the formula

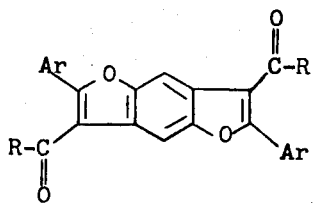

(I)

wherein:

R represents alkoxy, aralkoxy, aryloxy, cycloalkoxy, hydroxyl, an oxygen atom linked to the radical Ar, or the group

$R_1$ and $R_2$ independently of one another denote hydrogen, alkyl, aralkyl or aryl, or together denote a saturated carbocyclic or heterocyclic ring and Ar denotes an aromatic-carbocyclic or aromaticheterocyclic radical, with the proviso that Ar denotes a substituted benzene radical if R represents $C_1$–$C_2$-alkyl, their preparation and their use as whitening agents.

Suitable alkoxy radicals are those with 1–20 C atoms, which are optionally monosubstituted by hydroxyl, halogen, nitrile and the like.

Suitable aralkoxy radicals are phenyl-$C_1$–$C_3$-alkoxy radicals.

Suitable aryloxy radicals are phenoxy radicals optionally substituted by phenyl or $C_1$–$C_4$-alkoxy.

Suitable cycloalkoxy radicals are cyclopentoxy, cyclohexoxy and methylcyclohexoxy.

Compounds preferred within the formula I are those corresponding to the formula

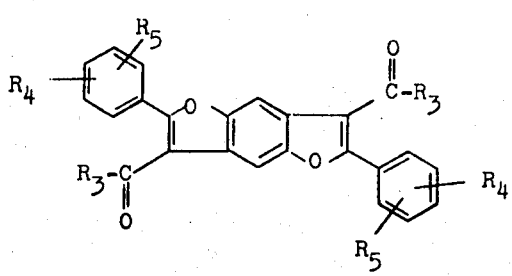

(II)

wherein $R_3$ denotes hydroxyl, alkoxy with 1–20 carbon atoms, benzyloxy, cycloalkoxy with 3–7 carbon atoms, the group

or an oxygen atom linked to the phenyl radical in the o-position, $R_4$ and $R_5$ independently of one another denote hydrogen, halogen, nitrile, phenyl, alkyl or alkoxy with 1–4 C atoms, phenoxy,

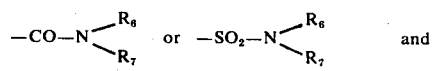

$R_6$ and $R_7$ independently of one another denote hydrogen or alkyl with 1–4 C atoms, with the proviso that $R_4$ and $R_5$ do not simultaneously denote hydrogen. Further compounds of importance are those of the formula I wherein R represents the

group and
Ar denotes phenyl and those of the formula I wherein:

R represents $C_3$–$C_{20}$-alkoxy, benzyloxy, cyclohexoxy or hydroxyl and
Ar denotes phenyl.

The compounds of the formula (I) are obtained by reaction of compounds which in their keto form correspond to the formula $$Ar-CO-CH_2-CO-R \quad (III)$$

in which:

Ar and R have the abovementioned meaning, with p-benzoquinone.

Compounds of the formula (III) are known, for example, from *J. Am. Chem. Soc.* 63, 2252 (1941). They can be prepared, for example, by the methods indicated in Organic Reactions, Vol. 1, 297–302, John Wiley & Sons, Inc., New York 1947, by reaction of arylcarboxylic acid esters with acetic acid esters or of arylcarboxylic acid esters with acetonitrile and subsequent alcoholysis, by acid splitting or ketone splitting of acylated β-keto-esters, by reaction of cyanoacetic acid esters with aromatic Grignard compounds and subsequent hydrolysis, by oxidation of β-aryl-β-hydroxypropionic acid esters with chromium trioxide, by addition of $H_2O$ to phenylacetylenecarboxylic acid and subsequent esterification and, preferably, by condensation of acetophenones with diethyl carbonate in the presence of sodium ethylate.

Examples of suitable compounds of the formula (III) are compounds of the formula

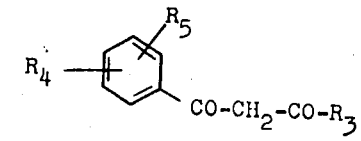

(IV)

and of the formula

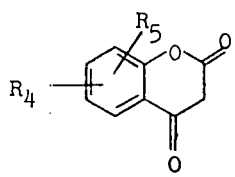

wherein:

$R_3$, $R_4$ and $R_5$ have the abovementioned meaning.

As examples there may be mentioned: benzoylacetic acid ethyl ester, propyl ester, butyl ester, hexyl ester, octyl ester, decyl ester, dodecyl ester, cyclopentyl ester, cyclohexyl ester, benzyl ester and phenyl ester, benzoylacetic acid amide, dimethylamide, diethylamide, morpholide and piperidide, p-methylbenzoylacetic acid methyl ester, butyl ester, hexyl ester, dimethylaminde, diethylamide and morpholide, p-chlorobenzoylacetic acid methyl ester, ethyl ester, hexyl ester, methylamide, diethylamide and piperidide, p-methoxybenzoylacetic acid ethyl ester, propyl ester, cyclohexyl ester, diethylamide and butylamide, p-ethoxybenzoylacetic acid ethyl ester and dimethylamide, p-cyanobenzoylacetic acid methyl ester, p-phenylbenzoylacetic acid methyl ester, ethyl ester, dimethylamide and piperidide, 3,5-dichloro-benzoylacetic acid methyl ester, butyl ester, cyclohexyl ester, amide, diimethylamide and diethylamide, p-bromobenzoylacetic acid methyl ester, p-phenoxybenzoylacetic acid, methyl ester, ethyl ester and amide, β-naphthoylacetic acid methyl ester, ethyl ester, amide and diethylamide, furoylacetic acid methyl ester, 4-hydroxycoumarin, 4-hydroxy-6-methylcoumarin, 4-hydroxy-8-methylcoumarin, 4-hydroxy-6-chlorocoumarin, 4-hydroxy-6-tert.-butylcoumarin, 4-hydroxy-6-bromocoumarin, 4-hydroxy-6-methoxycoumarin, 4-hydroxy-7-methoxycoumarin, 4-hydroxy-6-phenylcoumarin, 4-hydroxy-6-cyclohexylcoumarin, 4-hydroxy-6-fluorocoumarin and 4-hydroxy-6,7-dichlorocoumarin.

A particularly simple process for the preparation of compounds of the formula (II), wherein $R_3$ represents alkoxy, cycloalkoxy, aryloxy or the group

starts from the particularly easily accessible compounds of the formula (II) wherein:

$R_3$ represents methoxy or alkoxy which are transesterified or trans-amidised with the corresponding alcohols or amines to give the desired compounds.

Compounds in which $R_3$ denotes hydroxyl are obtainable by saponification of the esters.

The compounds of the formula (I) can be prepared in either one step or two steps.

In the two-step process, the starting material (III) is first added onto the p-benzoquinone in the presence of a base such as, for example, triethylamine, pyridine, piperidine, sodium methylate, a trace of NaOH or KOH, in an inert solvent, at temperatures between 20° and 120°C, preferably between 40 and 80°C. Suitable solvents are alcohols such as methanol or ethanol, dioxane or aromatic hydrocarbons such as benzene, toluene or xylene. The resulting product is subsequently cyclised in one of the solvents mentioned — aromatic hydrocarbons which permit azeotropic distillation of the water of reaction being preferred — in the presence of an acid catalyst such as mineral acids in the form of $H_2SO_4$, $H_3PO_4$ or polyphosphoric acid, or metal chlorides, at temperatures between 50° and 150°C. The preferred catalyst is anhydrous zinc chloride.

In the one-step process, the starting material (III) is reacted direct with p-benzoquinone in an organic solvent such as methanol, ethanol, dioxane or diethyl ether, in the presence of the acid catalysts mentioned and at the boiling point of the solvent, to give the benzodifurane compounds. The system zinc chloride/alcohol is preferred. The benzodifurane compounds (I) can easily be isolated from the reaction mixtures by crystallisation because of their low solubility.

The synthesis of the compounds (I), in which R denotes an oxygen atom bonded to the Ar group, is most advantageously carried out in two steps. The hydroxycoumarin compounds (V) are first reacted with p-benzoquinone analogously to what has been described above in connection with the two-step process and the resulting product is cyclised with mineral acids such as sulphuric acid, phosphoric acid or hydrochloric acid, and strong organic acids, such as sulphonic acids, optionally in the presence of an inert organic solvent such as benzene, toluene or xylene, at temperatures of 50° to 200°C.

The reaction is preferably carried out in concentrated sulphuric acid at 40° – 80°C.

A further subject of the present invention is the use of benzodifurane compounds of the formula

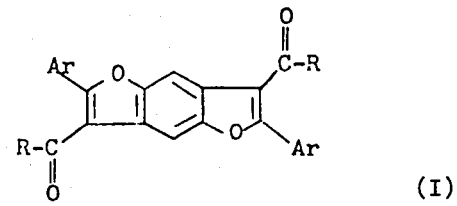

wherein:

R denotes alkoxy, aralkoxy, aryloxy, cycloalkoxy, hydroxyl, and oxygen atom bonded to the radical Ar or the group

$R_1$ and $R_2$ independently of one another denote hydrogen, alkyl, aralkyl or aryl or together denote a saturated carbocyclic or heterocyclic ring and Ar denotes an aromatic-carbocyclic or aromaticheterocyclic radical as UV absorbers and as whitening agents for organic materials.

By organic materials there are to be understood natural fibrous materials, such as cotton and wool, but above all synthetic fibre-forming polymers, for example polyesters, polyamides, polyurethanes, polyolefines (polyethylene or polypropylene), polyvinyl acetate, polyvinyl chloride, polyvinylidene chloride, polyacrylonitrile, modified polyacrylonitrile, cellulose triacetate, cellulose 2½-acetate and polystyrene.

For the purpose of whitening, the benzodifurane compounds can be used in the customary manner, for example in the form of solutions or suspensions in organic solvents or as aqueous dispersions, to which customary dyeing auxiliaries can be added. Above all, however, they are very successfully incorporated into spinning compositions and moulding compositions or added to the monomers intended for the preparation of plastics, or to a precondensate thereof. In addition they can be used, optionally in combination with bleaching agents, for the preparation of washing agents. Depending on the process in which they are to be employed, the concentration can be 0.005 to 0.5%, and preferably 0.01 to 0.2%, of the benzodifurane compounds according to the invention, relative to the material to be whitened.

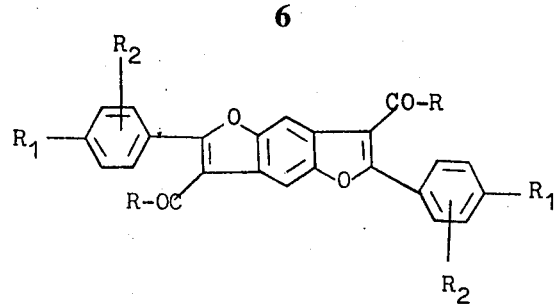

| Example No. | R | $R_1$ | $R_2$ | Fluorescence in the solvent |
| --- | --- | --- | --- | --- |
| 2 | $-OCH_3$ | $-H$ | $-H$ | blue (dioxane) |
| 3 | $-OCH_3$ | $-Cl$ | $-H$ | blue (DMF) |
| 4 | $-O-CH_3$ | $-Cl$ | $-Cl$ (o) | blue (trichlorobenzene) |
| 5 | $-O-CH_3$ | $-C\equiv N$ | $-H$ | light blue (DMF) |
| 6 | $-O-C_2H_5$ | H | $-CN$ (m) | blue (DMF) |
| 7 | $-OCH_3$ | $-C_6H_5$ | $-H$ | light blue (DMF) |
| 8 | $-OC_2H_5$ | $-OCH_3$ | $-H$ | dark blue (dioxane) |
| 9 | $-OCH_3$ | $-O-$ | $-H$ | blue (DMF) |
| 10 | $-OCH_3$ | $-H$ | $-OCH_3$ (o) | light blue (dioxane) |
| 11 | $-OCH_3$ | $-SO_2NH_2$ | $-H$ | blue (DMF) |

To improve the whitening effect it is frequently advisable to add to the benzodifurane compounds according to the invention water-insoluble, heat-stable and sublimationresistant shading dyestuffs in concentrations of 0.1 to 1.0 % (relative to the whitener). Suitable shading dyestuffs are:
Pigment Violet 23, C.I. 51,319
Pigment Blue 15, C.I. 74,160
Pigment Violet 40
Solvent Violet 13, C.I. 60,725
Solvent Blue 97
Solvent Violet 36
Solvent Red 52, C.I. 68,216

EXAMPLE 1

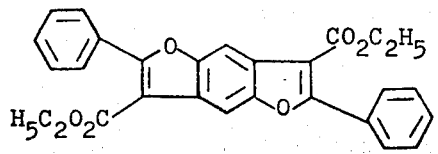

5 g of p-benzoquinone and 9,6 g of benzoylacetic acid ethyl ester are dissolved in 25 ml of abosulute ethanol and the mixture is warmed under reflux for 30 minutes. 30 ml of a 50% strength solution of anhydrous zinc chloride in absolute ethanol are then added to the reaction solution, the reaction mixture is warmed for 1 hour under reflux and cooled and the product which has precipitated is filtered off, washed with ice-cold ethanol and recrystallised from glacial acetic acid; yield 8.5 g (56.3%). The substance has a deep blue fluorescence when dissolved in dioxane, and displays a strong brightening effect when incorporated into polyurethane filaments.

EXAMPLES 2 – 11

The benzodifurane compounds of Examples 2 – 11 are obtained according to the method indicated in Example 1:

EXAMPLE 12

5.0 g of the compound obtained according to Example 7 and 25 g of potassium hydroxide, in a mixture of 50 ml of diethylene glycol dimethyl ether and 25 ml of water, are boiled for 20 hours under reflux. The reaction mixture is then poured into 1 liter of water and acidified with dilute hydrochloric acid. The precipitate is filtered off and recyrstallised from dimethylformamide. 3.5 g (74% of theory) of the compound of the formula

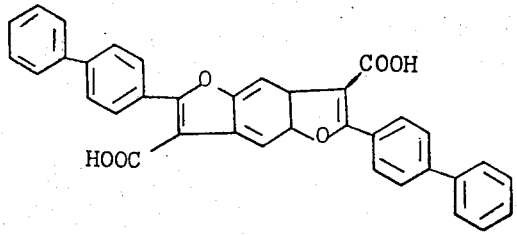

are obtained. The compound shows a green-blue fluorescence in dimethylformamide.

EXAMPLE 13

A compound of the formula

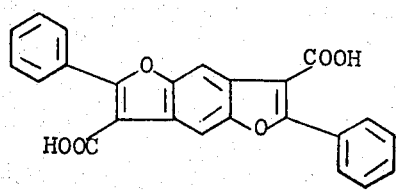

is obtained by the method indicated in Example 12 from the compound obtainable according to Example 1; fluorescence in dimethylformamide: blue.

EXAMPLE 14

A compound of the formula

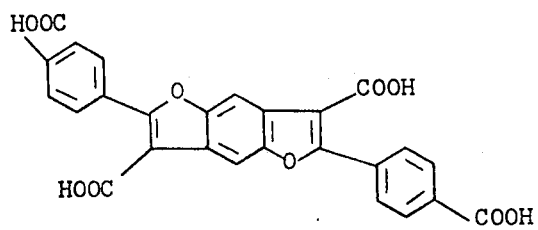

is obtained by the method indicated in Example 12 from the compound obtainable according to Example 5; fluorescence in dimethylformamide: blue.

EXAMPLE 15

4.0 g of the compound from Example 1 in 100 g of decanol are warmed with 1 g of sodium methylate for 3 hours to 110°C, the reaction mixture is then neutralised with acetic acid, the excess alcohol is distilled off in a high vacuum, the residue is boiled up in 250 ml of chloroform, the mixture is filtered and the filtrate is concentrated. After trituration with petroleum ether, 4.2 g (70% of theory) of the di-decyl ester are obtained. The substance fluoresces deep blue in dioxane.

EXAMPLES 16 – 20

Using the method described in Example 15, the compounds indicated in the table are prepared from the corresponding starting compounds by trans-esterification or transamidation, or conversion of an acid into the amide according to known methods.

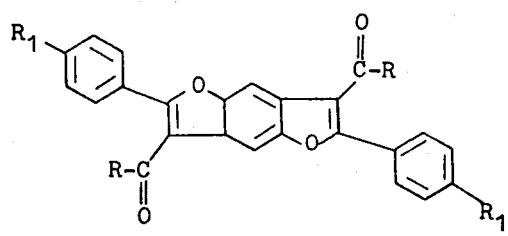

| Example No. | R | $R_1$ | Starting compound | Fluorescence in |
|---|---|---|---|---|
| 15 | $-OC_{10}H_{23}$ | H | Example 1 | blue (dioxane) |
| 16 | $-NH_2$ | $-CONH_2$ | Example 14 | blue (DMF) |
| 17 | $-NHC_2H_5$ | $-H$ | Example 1 | blue (DMF) |
| 18 | $-OCH(CH_3)_2$ | $-H$ | Example 1 | blue (dioxane) |
| 19 | $-OC_4H_9$ | $-H$ | Example 1 | blue (dioxane) |
| 20 | $-NHCH_3$ | $-OCH_3$ (o) | Example 21 or 10 | blue (DMF) |

EXAMPLE 21 a. Addition of 4-hydroxycoumarin to p-benzoquinone 16.2 g of 4-hydroxycoumarin and 10.8 g of p-benzoquinone are dissolved in 35 ml of dioxane. The solution is slowly added dropwise, whilst cooling with ice, . . . . 0.3 g of piperidine diluted with 5 ml of dioxane, and after the exothermic reaction has subsided the reaction mixture is warmed to 60°C for 2 hours. The reaction mixture is filtered warm and subsequently cooled. The adduct which has precipitated is filtered off, washed with dioxane and recrystallised from dioxane/cyclohexane; yield 10.2 g (44% of theory).

b. Cyclisation 10 g of the adduct obtained above, in 50 ml of concentrated sulphuric acid, are warmed to 70°C for 2 hours. The reaction mixture is poured onto ice and the prpecipitate is filtered off, washed with water until neutral and recrystallised from dimethylformamide; yield 6.4 g (70% of theory).

Use example A:

200 g of polyethylene terephthalate are fused in a container at 280°C, under a nitrogen atmosphere, and 0.4 g of the compound of Example 7 is added. The brightener is stirred into the polyester until a homogeneous solution results. 4 g of titanium dioxide are then added as a delustering agent and the total mass is stirred again, until a homogeneous mixture results. The latter is spun by means of a spinneret to give a filament which is cooled with water, stretched and wound up on bobbins in the usual way. The filaments show brilliant brightening.

If instead of the abovementioned compound one of the compounds of Examples 2, 3 or 5 is used, similar white effects are obtained.

Use example B:

100 G of polyester granules are powdered with 0.02 g of the compound from Example 17 or 18 in a mixing apparatus, and converted into injection mouldings. The mouldings have a substantially improved appearance, in respect of degree of whiteness, as compared to mouldings which have not been brightened.

Use example C:

A stock solution is prepared from 10 g of polyacrylonitrile, 85 g of dimethylformamide and 5 g of the compound from Example 7. This is added to a customary polyacrylonitrile spinning solution, in such amount that the concentration of the brightener in the spun polyacrylonitrile material is 0.25%. The spinning solution is then spun in the usual way. The fibre material is additionally bleached with sodium chlorite and shows a very good brightening effect when compared with a fibre which has not been brightened.

Use example D:

A fabric of polyethylene glycol terephthalate filaments bleached in the usual way is impregnated with a dispersion which contains 1 g/l of the compound of Example 7. The textile material thus treated is squeezed out between rollers until the liquid it retains amounts to only 70% of its dry weight and is then exposed to a hot air treatment at 200°C for 30 seconds.

The fabric treated in this way has a very good degree of whiteness.

The dispersion indicated in Example D can be prepared as follows:

2 parts of the compound from Example 7, 3 or 5 are mixed with 2 parts of a highly sulphonated castor oil, 8 parts of sodium (dioctylphenyl polyglycol ether)-oxyacetate containing 40 ethoxy groups per molecule, and 80 parts of water. This mixture is finely ground on a bead mill until about half of the particles are of size 0.5–1µ, diluted with water to a concentration of approx. 10% relative to the particular compound, and homogenised.

Use example E:

A fabric of polyethylene glycol terephthalate filaments is treated, using a ratio of 1:20, in a liquor which contains 1 g/l of sodium chlorite and 0.05 g/l of the compound from Example 7, 3 or 5 in a dispersed form.

The bath is brought to 125°C over the course of 45 minutes in an HT dyeing apparatus and the textile goods are treated at this temperature for a further 45 minutes.

After rinsing and drying, the fabric treated in this way displays a very good degree of whiteness which is substantially more brilliant than that achieved by treatment with sodium chlorite.

Use example F:

6.0 Kg of dimethylterephthalate and 5 litres of ethylene glycol are mixed at room temperature in a reaction vessel which can be evacuated and is provided with a gas inlet, heater and mechanical stirrer, and the following substances are added successively:

1.5 g of titanium dioxide as a delustering agent
0.24 g of a standard catalyst and
0.24 g of a whitener/dyestuff mixture which is taken from a previously prepared stock batch composed of:
100 Parts by weight of the compound from Example 7,
0.48 part by weight of Pigment Violet 23, C.I. 51,319 and
0.12 part by weight of Pigment Blue 15, C.I. 74,160.

The reaction is commenced by heating for 3 hours at 180°–220°C and the precondensation is then carried out by further heating at 250°C for 45 minutes and the polycondensation by heating at 275°C for 3.5 hours at from 1 mm Hg downwards under nitrogen. The polyester granules which are then isolated in a known manner possess, as compared to granules prepared without a tinted whitener, a brilliant high degree of whiteness of a slightly greenish-tinged shade.

We claim:

1. A benzodifuran compound of the formula

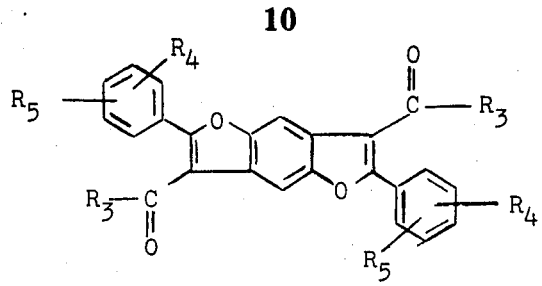

wherein:

$R_3$ denotes hydroxyl, alkoxy with 1 to 20 carbon atoms, cycloalkoxy with 3 to 7 carbon atoms, benzyloxy or the group

$R_4$ and $R_5$ independently of one another denote hydrogen, cyano, phenyl, alkyl with 1 to 4 carbon atoms, alkoxy with 1 to 4 carbon atoms, phenoxy

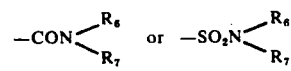

$R_6$ and $R_7$ independently of one another denote hydrogen or alkyl with 1 to 4 carbon atoms, with the proviso that $R_4$ and $R_5$ do not simultaneously denote hydrogen.

2. Benzofurane compound of the formula

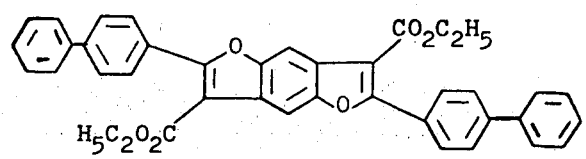

* * * * *